(12) United States Patent
Steiger

(10) Patent No.: US 6,455,034 B1
(45) Date of Patent: Sep. 24, 2002

(54) METHOD FOR INHIBITING THE DEVELOPMENT OF BODY ODORS

(75) Inventor: Fred H. Steiger, East Brunswick, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 08/322,741

(22) Filed: Oct. 13, 1994

Related U.S. Application Data

(63) Continuation of application No. 08/008,857, filed on Jan. 25, 1993, now abandoned, which is a continuation of application No. 07/860,113, filed on Mar. 30, 1992, now abandoned, which is a continuation of application No. 07/732,372, filed on Jul. 18, 1991, now abandoned.

(51) Int. Cl.⁷ .............................. A61L 9/00; A61L 9/01; A61L 9/04; A61L 11/00
(52) U.S. Cl. .................... 424/76.1; 424/76.4; 424/76.5; 424/76.6; 424/76.7; 424/401; 424/422; 424/430; 424/432
(58) Field of Search ................................. 424/401, 422, 424/430, 432, 76.1, 76.4, 76.5, 76.6, 76.7

(56) References Cited

U.S. PATENT DOCUMENTS

| | | | | |
|---|---|---|---|---|
| 2,815,260 A | * | 12/1957 | Melander et al. | 604/359 |
| 3,091,241 A | * | 5/1963 | Kellett | 128/270 |
| 3,172,817 A | * | 3/1965 | Leupold | 167/90 |
| 3,317,372 A | * | 5/1967 | Hart | 424/76.21 |
| 3,690,321 A | * | 9/1972 | Hirschman | 604/359 |
| 3,794,034 A | * | 2/1974 | Jones, Sr. | 604/360 |
| 3,995,636 A | * | 12/1976 | Murray | 128/285 |
| 4,186,743 A | * | 2/1980 | Steiger | 604/359 |
| 4,244,059 A | * | 1/1981 | Pflaumer | 424/76.3 |
| 4,273,786 A | | 6/1981 | Kraskin | 424/319 |
| 4,356,190 A | | 10/1982 | Kraskin | 424/319 |
| 4,641,605 A | * | 2/1987 | Gordon | 119/171 |
| 4,675,014 A | * | 6/1987 | Sustmann | 604/375 |
| 4,957,063 A | * | 9/1990 | Heitfeld | 119/1 |
| 5,037,412 A | * | 8/1991 | Tanzei et al. | 604/359 |
| 5,039,481 A | * | 8/1991 | Pacifici et al. | 424/76.21 |
| 5,097,799 A | * | 3/1992 | Heitfeld et al. | 119/172 |
| 5,122,407 A | * | 6/1992 | Yeo et al. | 604/359 |

FOREIGN PATENT DOCUMENTS

| | | | |
|---|---|---|---|
| DE | 0 131 269 | 7/1984 | |
| DE | 0 158 092 | 2/1985 | |
| DE | 0 424 845 A2 | 10/1990 | |
| EP | WO 86/05388 | 9/1986 | |
| GB | 0 019 371 | 4/1980 | ........... A61L/15/00 |
| GB | 2 083 748 A | 9/1981 | |

* cited by examiner

Primary Examiner—Thurman K. Page
Assistant Examiner—H. Sheikh
(74) Attorney, Agent, or Firm—James P. Barr

(57) ABSTRACT

Methods, compositions and products are described which inhibit the development of odor in excreted body fluids by odor-causing cations.

20 Claims, No Drawings

METHOD FOR INHIBITING THE DEVELOPMENT OF BODY ODORS

This is a continuation, of application Ser. No. 08/008,857, filed Jan. 25. 1993, now abandoned, which is a continuation of application Ser. No. 07/860,113, filed Mar. 30, 1992, now abandoned, which is a continuation of application Ser. No 07/732,372, filed Jul. 18, 1991, all now abandoned.

BACKGROUND OF THE INVENTION

The invention relates to methods, compositions and articles of manufacture useful for inhibiting the development of undesirable body odors. In particular, it relates to a method for inhibiting the development of odor in excreted body fluids by precipitating odor-causing cations in body fluids, thereby effectively causing deodorization. Although the method of the invention effectively inhibits or suppresses the development of malodors in all kinds of excreted body fluids, it is especially effective in menstrual fluid.

BRIEF DESCRIPTION OF THE PRIOR ART

The problem of the development of undesirable body odor arising from excreted body fluids such as urine, perspiration and menstrual fluid is well known. In U.S. Pat. Nos. 4,273,786, and 4,356,190, Kraskin teaches using aminopolycarboxylic acid compounds such as ethylenediaminetetraacetic acid (EDTA) and the salts thereof to inhibit the formation of odoriferous fatty acids. Kraskin hypothesized that the amino compounds act by removing the necessary metallic co-factor ions for the enzymatic production of the fatty acids.

However, the method taught by Kraskin has several drawbacks. First, it has been found that although EDTA and the like effectively deodorize urine, such compounds are much less effective in deodorizing other body fluids, such as menstrual fluid. Menstrual fluid generally has three odorants: amines, fatty acids (i.e., isobutyric acid), and sulfides. As menstrual fluid ages, its pH remains constant. However as urine ages, its pH increases (i.e., it becomes more basic). The aminopolycarboxylic acid compounds taught by Kraskin effectively attack odor produced by urine because increasing pH increases their effectiveness. However, for this same reason, EDTA and the other agents taught by Kraskin do not work as well on malodors which develop in menstrual fluid and perspiration. Accordingly, it would be desirable to develop a method for inhibiting the development of odors in excreted body fluids which is independent of the pH of the body fluid. Menstrual fluid contains additional ions, such as iron cations, which selectively and preferentially chelate with compounds such as EDTA, thereby reducing their effectiveness as deodorants. Thus, it also would be desirable to develop a method to inhibit the development of odor in excreted body fluid which avoids the deleterious effect of the extraneous ions found in some body fluids.

The present invention provides a method which effectively inhibits the development of odor in urine, perspiration, and menstrual fluid, wherein the effectiveness of the method is independent of the pH of the body fluid. The novel method of the present invention is also generally not affected by the presence of additional ions, such as iron. These characteristics are especially valuable for inhibiting the development of odor in menstrual fluids. In addition, the method may be easily employed using a variety of means, and applied to variety of receptacle devices adapted to receive excreted body fluids. Furthermore, the method of the invention effectively inhibits the development of malodors in body fluids in a safe and inexpensive manner, and without adverse effects on human subjects.

SUMMARY OF THE INVENTION

The method of this invention relates to a product incorporating means for inhibiting the development of odor in absorbed excreted body fluids. According to the method of this invention, absorbed body fluids are contacted with a salt, the salt having an anion capable of forming a complex with the metallic co-factor ions in the body fluids that is substantially-insoluble in the body fluid, and the salt being present in an amount effective to provide sufficient anion to complex substantially all of the cation.

The method of this invention also relates to inhibiting the development of odor in excreted body fluids, wherein the method comprises contacting the body fluids with a salt, the salt having can anion capable of forming a precipitate with metallic co-factor ions in the body fluids, and e anion being present in an amount effective to prevent the formation of odor, by precipitating a substantial portion of the cations.

More particularly, according to the method of this invention, the formation of odor in excreted body fluids is inhibited by contacting the body fluids with a salt having a precipitating agent for calcium and/or magnesium cations, where the precipitating agent has a solubility product constant with calcium and/or magnesium cations of less than about $1 \times 10^{-7}$, and where the salt is present in an amount effective to provide sufficient precipitating agent to precipitate a substantial portion of the calcium and magnesium cations.

The method of this invention effectively suppresses the development of odor in excreted body fluids, and thus, in effect, deodorizes the body fluids. The method is especially effective in removing calcium and magnesium cations from excreted body fluids, which are thought to be two odor-causing cations present in body fluids.

Sufficient amount of the salt is present in the product to provide sufficient anion to complex with substantially all of the metallic co-factor ions.

DETAILED DESCRIPTION OF THE INVENTION

The method of the present invention comprises contacting body fluids with a salt having an anion capable of forming a substantially-insoluble complex with the odor-causing cations found in excreted body fluids. Odor-causing cations specifically include, but are not limited to, calcium and magnesium cations or a mixture thereof.

According to the method of this invention, the development of odors is inhibited by using the solubility product constant, Ksp, of a metal ionic complex comprised of the anion from the salt and cations from the body fluid. When the solubility product of the concentration of the cations and the anion exceeds the solubility product constant, a metal ionic complex forms that is substantially-insoluble in the body fluid. The method of the invention uses a salt having an anion capable of forming a substantially-insoluble metal ionic complex with odor-causing cations, in an amount effective to provide sufficient anion to complex substantially all of the cations, so that essentially all of the metal ionic complex precipitates. This precipitation effectively removes the odor-causing cations from the body fluid and substantially prevents them from reacting further.

If two solutions, each containing one of the ions of a slightly soluble metal ionic complex, are mixed together, no precipitation takes place unless the solubility product of the ion concentrations in the mixture is greater than the solubility product constant. Thus, it is desirable to utilize a salt comprising an anion where the solubility product constant of the anion and the cation is smaller than a predetermined critical value, so that the anion and cation will form a substantially insoluble complex that readily precipitates. Thus, it is preferable to utilize a metal ionic complex which has a relatively small solubility product constant because such a complex will readily precipitate and will be essentially insoluble in solution.

The solubility product constant, Ksp, is defined herein to mean, in any solution in equilibrium with a slightly soluble ionic compound, the product of the concentrations of the ions, each raised to a power equal to its coefficient in the net ionic equation for the solution process. These concentrations usually are expressed as moles of solute per liter of solution. The solubility product constant is dependent upon temperature and, thus, is usually reported at a specific temperature.

For example, the solubility product constant for calcium fluoride ($CaF_2$) is $3.95 \times 10^{-11}$ at 26° C. *CRC Handbook of Chemistry and Physics*, 63rd Edition, (1982–83), at B-242. The equation for this solubility product constant is as follows:

$$[Ca^{++}] \times [F^-]^2 = 3.95 \times 10^{-11}$$

When the concentration of either ion in solution causes the calculation to exceed the solubility product constant, the metal ionic complex $CaF_2$ will precipitate. In this manner, the addition of a salt containing fluoride anions can remove calcium, magnesium and/or other odor-causing cations from the excreted body fluid.

Examples of other calcium and magnesium salts with relatively small solubility product constants include:

| SALT | SOLUBILITY PRODUCT CONSTANT |
| --- | --- |
| Calcium Oxalate | $2.6 \times 10^{-9}$ (25.0° C.) |
| Magnesium Fluoride | $6.4 \times 10^{-9}$ (27.0° C.) |
| Magnesium Ammnonium Phosphate | $2.5 \times 10^{-13}$ (25.0° C.) |

*CRC Handbook of Chemistry and Physics*, 63rd Edition, (1982–83) at B-242. The solubility product constants for additional salts are readily available from the above-cited source and from several other sources, including, for example, *Lange's Handbook Of Chemistry*, 13th Ed., Editor, John A. Dean, 1985, pp. 5–7 through 5–12. Solubility product constants are also easily determined by one skilled in the art of analytic or inorganic chemistry.

The term salt is defined herein to mean a composition comprised of at least one cation and one anion. Suitable salts comprise at least one anion selected from the group consisting of fluoride, phosphate, carbonate, oxalate, and tartrate. Preferred anions include fluoride, phosphate and oxalate anions. Fluoride anions are most preferred for precipitating calcium and magnesium ions because the solubility product constant for the metal ionic complex comprised of fluoride anions and either of these cations is relatively small. Thus, the complexes readily precipitate. It should be noted that the term precipitating agent as used herein means at least one anion capable of forming a precipitate with an odor-causing cation such as magnesium or calcium.

Of course, the suitability of a particular anion depends on its solubility product constant with the cations of the body fluid. However, the anion's suitability also depends on additional factors such as the compatibility of the anion with other components of catamenial and incontinence products which may be used in conjunction with the present invention, and the absence of irritation to the user.

Suitable salts include sodium fluoride, potassium fluoride, and sodium ammonium phosphate, among others. Sodium fluoride is preferred.

The critical value for the solubility product constant of a slightly soluble metal ionic complex, which would determine whether or not a particular combination will be effective as a deodorant, is readily determined by experimentation by one skilled in the art. A substantially-insoluble complex as used herein means a complex having a solubility product constant that is small enough so that at least about 90% of the complex forms a precipitate when in solution. It has been determined that in order to effectively inhibit the development of odors caused by either calcium or magnesium cations, the solubility product constant of an anion with calcium and/or magnesium cations should be smaller than, i.e., less than, about $1 \times 10^{-7}$ at about 25° C. (For example, a solubility product constant of $1 \times 10^{-8}$ is smaller than or less than $1 \times 10^{-7}$.)

The salts are to be used in such amounts as to provide anion in a concentration of from at least about 0.01% to about 10% by weight in said body fluid. The upper limit is dictated by practical considerations, including the avoidance of adverse health effects. Generally, adequate inhibition of odor is obtained at levels of about 5%. The preferred amounts depend on the purpose, place and method of application and on the particular salt used. For example, if the method is used in conjunction with an absorbent catamenial and incontinence product, higher concentrations will be required. For control of menstrual malodor, anion concentration of at least about 3% by weight in the menstrual fluid is desirable, and 7% is preferred.

In order to inhibit odor effectively, it is desirable to add enough salt so that the concentration of anion is sufficient to complex or precipitate a substantial portion, i.e., at least about 80%, of the odor-causing cations in solution in the body fluid. It is more preferred to add enough salt so that the concentration of anion is sufficient to complex or precipitate at least about 90% of the odor-causing cations in solution in the body fluid. It is even more preferred to add enough salt so that the concentration of anion is sufficient to complex or precipitate at least about 95% of the odor-causing cations. It is most preferred to add enough salt and anion to complex or precipitate substantially all of the odor-causing cations present in the body fluid. Substantially all of the odor-causing cations means at least about 98% of such cations.

The method may be applied to any receptacle device adapted to receive excreted body fluid. For example, to inhibit the formation of malodors in menstrual fluid, the salt is conveniently applied to catamenial products or other materials which may receive the fluid such as bed pads, or clothing. By catamenial products is meant products adopted to receive menstrual fluid, such as sanitary napkins, tampons, and panty liners. Such catamenial products usually consist of a core of one or more layers of highly absorbent, relatively dense materials which have a fluid permeable, soft, knitted, woven or non-woven wrapper. The cores are usually made of layers of fibers such as carded cotton webs, air-layered cellulosic fiber webs, or like materials, but may be made of newer synthetic materials such a synthetic polymer foams and fibers.

Additional receptacle devices adapted to receive excreted body fluids include incontinence products such as diapers, diaper liners, incontinence pads and bed pads. The term incontinence product is meant to include any device adapted to receive human discharges or evacuations.

The salt may be applied to the sites of formation of the undesirable body odors in various ways. Most generally the salt may be applied in a manner so that it is present on the body facing surface of, or proximate to the body facing surface of, any receptacle device adapted to receive excreted body fluid. Although the salt may be distributed uniformly through the receptacle adapted to receive the body fluid, it is generally more desirable to place it on the surface that is closest to the body and the excreted fluid, or proximate thereto. Thus, salt is preferably applied to the surface of the absorbent cores of the catamenial products in such a manner that the salt is present on the surface thereof in an amount ranging from about 0.001 g per square inch to about 0.1 g per square inch. Such amounts are likely to provide the desired concentration in terms of the amount of salt to total excreted body fluid. A preferred range for catamenial products is from about 0.02 to about 0.06 g per square inch.

The salt may be applied to the receptacle devices during manufacture or use. When applied during manufacture, it may be applied by spraying either in an aqueous spray or aerosol spray, padding, soaking, or dusting or any known method for applying materials thereto. A spray may employ propellants or inert solvents. In addition, the salt may be applied to the receptacle device prior to use in dry powder form.

The method of this invention may also be applied to animal litter compositions. Animal litter is a composition which is used by house pets for the deposition of urine and feces. The pets which use such a material may include gerbils and mice as well as cats.

With prolonged use, the animal litter develops an unpleasant smell which may make it necessary to change the animal litter even though the absorption capacity of the litter has not been exhausted.

The odor of cat urine, for example, is clinging and persistent. Perfuming agents may be used to neutralize these disagreeable odors but these perfuming agents tend to evaporate with time. Thus, after a certain time, odor masks are exhausted and the odors reappear.

The aim of this embodiment of this invention is to permit the longer use of animal litter by delaying the onset of odor and, thereby, reduce its intensity.

Animal litter may be constituted of either inorganic or organic particles. The inorganics may consist of any one of a number of materials or mixtures of materials, such as perlite, pumice sand, and a variety of ground dried clays, including attapulgite, montmorillonite, bentonite and Fullers earth. Other suitable absorbent materials known to those of skill in the art may also be used.

The organic absorbents may be single materials or mixtures of materials such as sawdust, wood flour, wood chips, oat hulls, or other suitable organic absorbent materials known to those of skill in the art.

A range of particle sizes is appropriate for the materials which are used as animal litter. A useful particle size for clay in this method, for example, is such that the particles will pass through a U.S. Sieve Number 8 screen and not through a U.S. Sieve Number 45 screen (about 2.3 mm to about 0.35 mm).

To reduce or eliminate unpleasant odor formation in animal litter, the absorbent material may be treated with an aqueous solution of sodium fluoride or any of the other materials which have a solubility product constant in the presence of calcium ion of $1 \times 10^{-7}$ or less.

Using sodium fluoride, for example, as a deodorizing treatment for animal litter, the dry powder is dissolved in water. The exact concentration of this solution is determined by the quantity of solution which is to be deposited on the animal litter.

The treatment should be conducted in such a way that at least 50% of the surface of the absorbent granules are covered with the solution and the animal litter after drying will have a sodium fluoride content of about 0.05% to about 0.5% by weight, preferably about 0.1% to about 0.3% by weight on inorganic absorbent particles and from about 0.2% to about 0.4% by weight on organic absorbent particles.

The solution may be applied by spraying with a conventional metering pump through a plurality of conventional spray nozzles onto an evenly distributed bed of absorbent particles. Preferably, the bed should be in the range of about 0.5 to about 1.5 inches in thickness.

An alternative application process for the uniform application of the spray has the particles conveyed by a conveyor belt to a point of free fall at which point the particles are sprayed with the solution.

The treated absorbent particles may be dried to a residual moisture content of about 10% or less by heating at a temperature as appropriate for the particles.

When used in a litter box and exposed to the urine and feces of animals, particles treated in the manner described will develop less odor than would similar particles which have not been so treated.

One example for determining the effectiveness of the present method for inhibiting the formation of undesirable odors in urine utilized organoleptic techniques well known in the art and as follows. Additional information regarding organoleptic testing techniques is also readily available. American Society for Testing and Materials *ASTM Manual on Consumer Sensory Evaluation*, Philadelphia, Pa. (1979).

EXAMPLE

The fluoride ion was chosen as the anion or precipitating agent to precipitate calcium cations in urine, since the solubility product constant of calcium fluoride is $3.4-3.95 \times 10^{-11}$. *CRC Handbook of Chemistry and Physics*, 63rd Edition, (1982–83), at B-242. A five percent solution of sodium fluoride was made in untreated river water. The phrase untreated river water indicates that the water used was obtained from a river and did not receive any pretreatment wherein fluoride ions were separately added. In addition, a five percent solution of tetrasodium ethylenediaminetetraacetic acid was similarly prepared to serve as a positive control. Untreated river water was utilized as a negative control.

The test was conducted using a catamenial product, i.e., a panty shield, which contained no sodium bicarbonate, fragrance, or other deodorizing additive. The following samples were sprayed over approximately eight square inches of the catamenial product as follows:

| CODE | QUANTITY (grams) | INGREDIENT |
| --- | --- | --- |
| A | 0.9 | Untreated river water |
| D | 0.3 | Na$_4$ EDTA |
| G | 0.9 | Na$_4$ EDTA |
| J | 0.3 | NaF |
| M | 0.9 | NaF |

The catamenial products were permitted to air-dry at room temperature. Then each product was inoculated with 2.0 ml of pooled fresh urine. The samples were then placed into individual covered glass jars and incubated at 37° C. for four hours. The samples in the jars were subsequently evaluated for odor by a panel consisting of thirteen to fifteen judges. Each judge ranked the five samples by placing them in the order of ascending odor intensity. A value of 5 indicated the sample with the strongest odor.

The same samples in their individual jars were then reincubated for seventeen hours and then retested.

The same samples were subsequently maintained at room temperature for forty-eight hours and again retested.

Tables I, II and III show the results of the three tests.

The results set forth in Table I indicate that the two EDTA salt samples (D and G) which acted as the positive controls were ranked as having higher odor levels than the water sample (A) which was the negative control. This conclusion renders the results of this test suspect.

The second test was conducted by a panel of thirteen judges. The results set forth in Table II indicate that the water sample (A) was found to be the most odoriferous. The only statistically significant difference in odor at the 95% level of confidence was between the water sample (A) and the sample containing 0.3 g of EDTA salt (D). Samples containing sodium fluoride were statistically indistinguishable from samples containing EDTA salt.

The third test was conducted by a panel of thirteen judges. The results set forth in Table III indicate that the water sample (A) was found to have the most odor. However, additional statistically significant differences are apparent. For example, each sample containing sodium fluoride (J and M) possessed significantly less odor than the water sample (A). Furthermore, the sample containing only 0.3 g of sodium fluoride (J) had significantly less odor than the sample having 0.9 g of the EDTA salt (G).

Although the method of the present invention is directed toward achieving the inhibition of the development of odor in excreted body fluids by removing calcium and magnesium cations therefrom, the invention is not limited to any particular theory and the preventative control may be achieved on any ion which is determined to be necessary for the formation of odoriferous compounds.

TABLE I

PANEL TESTING SAMPLE RANKING REPORT
RANK OF SAMPLES

| Panelist Number | A | D | G | J | M |
|---|---|---|---|---|---|
| 62 | 3.0 | 4.0 | 5.0 | 1.0 | 2.0 |
| 161 | 3.0 | 1.0 | 2.0 | 4.0 | 5.0 |
| 957 | 3.0 | 2.0 | 5.0 | 4.0 | 1.0 |
| 958 | 4.0 | 3.0 | 5.0 | 2.0 | 1.0 |
| 635 | 4.0 | 3.0 | 5.0 | 2.0 | 1.0 |
| 504 | 4.0 | 3.0 | 1.0 | 5.0 | 2.0 |
| 114 | 2.0 | 1.0 | 5.0 | 3.0 | 4.0 |
| 503 | 1.0 | 2.0 | 4.0 | 3.0 | 5.0 |
| 111 | 2.0 | 1.0 | 4.0 | 5.0 | 3.0 |
| 141 | 1.0 | 2.0 | 5.0 | 4.0 | 3.0 |
| 19 | 1.0 | 4.0 | 2.0 | 3.0 | 5.0 |
| 480 | 4.0 | 2.0 | 5.0 | 1.0 | 3.0 |
| 936 | 3.0 | 1.0 | 5.0 | 2.0 | 4.0 |
| 978 | 1.0 | 5.0 | 4.0 | 3.0 | 2.0 |
| 969 | 1.0 | 2.0 | 4.0 | 5.0 | 3.0 |
| TOTAL FRIEDMAN RANK SUMS | 37.0 | 36.0 | 61.0 | 47.0 | 44.0 |

RANK DIFFERENCE TABLE

|  | A | D | G | J |
|---|---|---|---|---|
| D | −1.0 | | | |
| G | 24.0 | 25.0 | | |

TABLE I-continued

| J | 10.0 | 11.0 | −14.0 | |
| M | 7.0 | 8.0 | −17.0 | −3.0 |

In a Friedman Rank Sum Difference Test with 15 subjects per test a rank sum difference must be greater than or equal to 18.60 for significance at the 80% level of confidence.

In a Friedman Rank Sum Difference Test with 15 subjects per test a rank sum difference must be greater than or equal to 21.30 for significance at the 90% level of confidence.

In a Friedman Rank Sum Difference Test with 15 subjects per test a rank sum difference must be greater than or equal to 23.63 for significance at the 95% level of confidence.

In a Friedman Rank Sum Difference Test with 15 subjects per test a rank sum difference must be greater than or equal to 28.19 for significance at the 99% level of confidence.

TABLE II

PANEL TESTING SAMPLE RANKING REPORT
RANK OF SAMPLES

| Panelist Number | A | D | G | J | M |
|---|---|---|---|---|---|
| 958 | 5.0 | 2.0 | 1.0 | 3.0 | 4.0 |
| 957 | 4.0 | 1.0 | 5.0 | 2.0 | 3.0 |
| 969 | 3.0 | 2.0 | 1.0 | 4.0 | 5.0 |
| 111 | 1.0 | 2.0 | 3.0 | 5.0 | 4.0 |
| 503 | 5.0 | 4.0 | 1.0 | 2.0 | 3.0 |
| 62 | 5.0 | 3.0 | 4.0 | 2.0 | 1.0 |
| 936 | 2.0 | 1.0 | 4.0 | 3.0 | 5.0 |
| 978 | 4.0 | 3.0 | 5.0 | 2.0 | 1.0 |
| 504 | 2.0 | 3.0 | 5.0 | 1.0 | 4.0 |
| 114 | 5.0 | 2.0 | 3.0 | 4.0 | 1.0 |
| 480 | 5.0 | 1.0 | 3.0 | 4.0 | 2.0 |
| 141 | 5.0 | 2.0 | 4.0 | 1.0 | 3.0 |
| 635 | 5.0 | 2.0 | 4.0 | 3.0 | 1.0 |
| TOTAL FRIEDMAN RANK SUMS | 51.0 | 28.0 | 43.0 | 36.0 | 37.0 |

RANK DIFFERENCE TABLE

|  | A | D | G | J |
|---|---|---|---|---|
| D | −23.0 | | | |
| G | −8.0 | 15.0 | | |
| J | −15.0 | 8.0 | −7.0 | |
| M | −14.0 | 9.0 | −6.0 | 1.0 |

In a Friedman Rank Sum Difference Test with 13 subjects per test a rank sum difference must be greater than or equal to 17.31 for significance at the 80% level of confidence.

In a Friedman Rank Sum Difference Test with 13 subjects per test a rank sum difference must be greater than or equal to 19.83 for significance at the 90% level of confidence.

In a Friedman Rank Sum Difference Test with 13 subjects per test a rank sum difference must be greater than or equal to 21.99 for significance at the 95% level of confidence.

In a Friedman Rank Sum Difference test with 13 subjects per test a rank sum difference must be greater than or equal to 26.24 for significance at the 99% level of confidence.

TABLE III

PANEL TESTING SAMPLE RANKING REPORT
RANK OF SAMPLEB

| Panelist Number | A | D | G | J | M |
|---|---|---|---|---|---|
| 958 | 2.0 | 4.0 | 5.0 | 1.0 | 3.0 |
| 141 | 3.0 | 1.0 | 5.0 | 2.0 | 4.0 |
| 957 | 4.0 | 5.0 | 2.0 | 3.0 | 1.0 |
| 62 | 5.0 | 1.0 | 4.0 | 3.0 | 2.0 |
| 480 | 5.0 | 3.0 | 2.0 | 4.0 | 1.0 |
| 978 | 5.0 | 4.0 | 3.0 | 1.0 | 2.0 |
| 19 | 5.0 | 4.0 | 3.0 | 1.0 | 2.0 |
| 503 | 5.0 | 3.0 | 4.0 | 2.0 | 1.0 |
| 145 | 5.0 | 4.0 | 3.0 | 1.0 | 2.0 |
| 144 | 5.0 | 4.0 | 2.0 | 1.0 | 3.0 |
| 635 | 4.0 | 3.0 | 5.0 | 1.0 | 2.0 |
| 111 | 5.0 | 3.0 | 4.0 | 1.0 | 2.0 |
| 936 | 1.0 | 4.0 | 3.0 | 2.0 | 5.0 |
| TOTAL FRIEDMAN RANK SUNS | 54.0 | 43.0 | 45.0 | 23.0 | 30.0 |

RANK DIFFERENCE TABLE

|   | A | D | G | J |
|---|---|---|---|---|
| D | −11.0 |  |  |  |
| G | −9.0 | 2.0 |  |  |
| J | −31.0 | −20.0 | −22.0 |  |
| M | −24.0 | −13.0 | −15.0 | 7.0 |

In a Friedman Rank Sum Difference Test with 13 subjects per test a rank sum difference must be greater than or equal to 17.31 for significance at the 80% level of confidence.

In a Friedman Rank Sum Difference Test with 13 subjects per test a rank sum difference must be greater than or equal to 19.83 for significance at the 90% level of confidence.

In a Friedman Rank Sum Difference Test with 13 subjects per test a rank sum difference must be greater than or equal to 21.99 for significance at the 95% level of confidence.

In a Friedman rank sum difference test with 13 subjects per test a rank sum difference must be greater than or equal to 26.24 for significance at the 99% level of confidence

What is claimed is:

1. A method for inhibiting the development of odor in menstrual fluid in a catamenial product having a body facing surface adapted to receive said menstrual fluid and a garment facing surface, said method comprising contacting said menstrual fluid with a salt, said salt having at least one anion which is capable of forming a precipitate with odor-causing magnesium or calcium cations in said menstrual fluid and which is selected from the group consisting of fluoride, phosphate, oxalate, and carbonate, said salt being present in an amount effective to prevent the formation of said odor by precipitating a substantial portion of said cations and wherein said salt is proximate to the body facing surface of said catamenial product.

2. The method of claim 1 wherein said anion is at least one anion selected from the group consisting of fluoride, and phosphate.

3. The method of claim 1 where at least 90% of said cations are precipitated.

4. The method of claim 1 where substantially all of said cations are precipitated.

5. The method of claim 1 where said precipitating agent comprises at least one anion selected from the group consisting of fluoride, and phosphate.

6. The method of claim 1 wherein said catamenial products are sanitary napkins, or panty liners.

7. A catamenial device having a body-facing surface and a garment facing surface comprising a member adapted to receive menstrual fluid in combination with an amount of salt having a least one anion which is capable of forming a precipitate with odor-causing calcium or magnesium cations in said menstrual fluid and which is selected from the group consisting of fluoride, phosphate, oxalate, and carbonate, said amount of said salt being sufficient to precipitate substantially all of said cation and wherein said salt is proximate to the body-facing surface of said catamenial device.

8. The device of claim 7 where said salt is placed at or proximate to the body-facing surface of said device.

9. The device of claim 7 which is a sanitary napkin.

10. The device of claim 7 which is a panty liner.

11. The method of claim 1 wherein said anion is selected from the group consisting of fluoride and oxalate.

12. The method of claim 1 wherein said salt is selected from the group consisting of sodium fluoride, potassium fluoride, and sodium ammonium phosphate.

13. The device of claim 7 wherein said anion is at least one anion selected from the group consisting of fluoride, phosphate and oxalate.

14. The device of claim 7 wherein said anion is selected from t-he group consisting of fluoride and oxalate.

15. The device of claim 7 wherein said salt is selected from the group consisting of sodium fluoride, potassium fluoride, sodium ammonium phosphate.

16. The method of claim 1 wherein said anion is fluoride.

17. The method of claim 1 wherein salt is sodium fluoride.

18. The device of claim 7 wherein said anion is fluoride.

19. The device of claim 7 wherein said salt is selected from the group consisting of sodium fluoride, potassium fluoride, and sodium ammonium phosphate.

20. The device of claim 18 wherein said salt is sodium fluoride.

\* \* \* \* \*